United States Patent
Feistel et al.

(10) Patent No.: US 11,596,664 B2
(45) Date of Patent: Mar. 7, 2023

(54) **PLANT EXTRACTS MADE OF *SIDERITIS* AND USE THEREOF TO BOOST COGNITIVE PERFORMANCE**

(71) Applicant: Finzelberg GmbH & Co. KG, Andernach (DE)

(72) Inventors: Björn Feistel, Andernach (DE); Bernd Walbroel, Königswinter (DE)

(73) Assignee: Finzelberg GmbH & Co. KG, Andermach (DE)

( * ) Notice: Subject to any disclaimer, the term of this patent is extended or adjusted under 35 U.S.C. 154(b) by 1902 days.

(21) Appl. No.: 14/656,084

(22) Filed: Mar. 12, 2015

(65) Prior Publication Data
US 2015/0182573 A1 Jul. 2, 2015

Related U.S. Application Data

(63) Continuation of application No. 13/818,655, filed as application No. PCT/EP2011/064687 on Aug. 26, 2011, now abandoned.

(30) Foreign Application Priority Data

Aug. 27, 2010 (EP) .................... 10174411

(51) Int. Cl.
*A61K 36/53* (2006.01)
*A23L 33/105* (2016.01)
*A61K 31/13* (2006.01)
*A61K 31/27* (2006.01)
*A61K 31/4015* (2006.01)
*A61K 31/445* (2006.01)
*A61K 31/473* (2006.01)
*A61K 31/48* (2006.01)
*A61K 31/4985* (2006.01)
*A61K 31/55* (2006.01)
*A61K 45/06* (2006.01)

(52) U.S. Cl.
CPC ............ *A61K 36/53* (2013.01); *A23L 33/105* (2016.08); *A61K 31/13* (2013.01); *A61K 31/27* (2013.01); *A61K 31/4015* (2013.01); *A61K 31/445* (2013.01); *A61K 31/473* (2013.01); *A61K 31/48* (2013.01); *A61K 31/4985* (2013.01); *A61K 31/55* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,262,162 A * | 11/1993 | Bormann | A23L 2/02 424/765 |
| 6,322,824 B1 | 11/2001 | Chatterjee et al. | |
| 2002/0150637 A1 | 10/2002 | Castillo et al. | |
| 2004/0067986 A1 * | 4/2004 | Sassover | A61P 19/02 514/355 |

FOREIGN PATENT DOCUMENTS

| | | |
|---|---|---|
| DE | 10 2004 032165 | 2/2006 |
| EP | 1634602 B1 | 9/2010 |
| GR | 1004608 B1 | 6/2004 |
| JP | 04-210642 | 7/1992 |
| WO | 99/40905 A2 | 8/1999 |
| WO | 00/57707 | 10/2000 |
| WO | 2011/076867 A2 | 6/2011 |

OTHER PUBLICATIONS

Tunalier et al, Antioxidant Properties and Phenolic Compounds od *Sideritis* SPecies, 2004, Chemistry of Natural Compounds, 40: 206-210.*
Mountain Tea 2019 https://www.fragrantica.com/news/MOUNTAIN-TEA-Sideritis-The-Humble-3706.html (Year: 2019).*
Tunalier et al., Antioxidant Properties andPhenolic Compositions of Sideritis Species, 2004, Chemistry of Natural Compounds, 40: 206-210.*
Sultana et al., Effect of Extraction Solvent/Technique on the Antioxidant Activity of Selected Medicinal Plant Extracts , 2009, Molecules, 14: 2167-2180.*
Gülcan Özkan, Antioxidant and Antibacterial Activities of Turkish Endemic Sideritis Extracts; Grasas y Aceites; vol. 56, Fasc. 1 (2005), pp. 16-20.
Brookmeyer et al., "Forecasting the global burden of Alzheimer's Disease," Johns Hopkins University, Department of Biostatistics Working Papers, Paper 130 (2007).
Bu, "Apolipoprotein E and its receptors in Alzheimer's disease: pathways, pathogenesis and therapy," Nat Rev Neurosci, 10(5):333-344 (May 2009).
Corder et al., "Gene dose of apolipoprotein E type 4 allele and the risk of Alzheimer's disease in late onset families," Science (New Series), 261(5123):921-923 (Aug. 13, 1993).
Dekosky et al., "Ginkgo biloba for Prevention of Dementia: A Randomized Controlled Trial," JAMA, 300 (19):2253-2262 (2008).
Dimpfel et al., "Source Density Analysis of Functional Topographical EEG: Monitoring of Cognitive Drug Action," Eur J Med Res, 1:283-290 (1996).
Kassi et al., "Greek Plant Extracts Exhibit Selective Estrogen Receptor Modulater(SERM)-like Properties," Journal of Agricultural and Food Chemistry, 52(23):6956-6961 (2004).

(Continued)

*Primary Examiner* — Terry A McKelvey
*Assistant Examiner* — Catheryne Chen
(74) *Attorney, Agent, or Firm* — Christensen Fonder Dardi; Andrew H. Auderieth; Peter S. Dardi

(57) ABSTRACT

The invention relates to aboveground plant parts of *Sideritis* ssp. or extracts produced therefrom for use to boost cognitive performance.

20 Claims, 6 Drawing Sheets

(56) References Cited

OTHER PUBLICATIONS

Kessler et al., "DemTect: Ein neues Screening Verfahren zur Unterstützung der Demenzdiagnostik (DemTect: A new screening test to support the diagnosis of dementia)," Psycho, 26:343-347 (2000) (English Summary on p. 347).

Knörle et al.,"Extrakte aus Sideritis ssp. (griechischer Bergtee): Innovative zentral aktive Pflanzenextrakte mit breitem Wirkprofil (Extracts from Sideritis ssp. (Greek mountain tea): Innovative plant extracts acting on the central nervous system and having a broad activity profile)," http://ibam.de/pics/Poster-Wolnzach-2009.pdf (viewed Jul. 8, 2010).

Kumar et al., "Effect of Indian Hypericum perforatum Linn on animal models of cognitive dysfunction," Journal of Ethnopharmacology, 72:119-128 (2000).

Lehr et al., "Population pharmacokinetic modelling of NS2330 (tesofensine) and its major metabolite in patients with Alzheimer's disease," British Journal of Clinical Pharmacology 64(1): 36-48 (2007).

Marks et al., "Triple Reuptake Inhibitors: A Premise and Promise," Psychiatry Investigation 5: 142-147 (2008).

Moore et al., "St. John's wort induces hepatic drug metabolism through activation of the pregnane X receptor," Proc Natl Acad Sci USA, 97(13)7500-7502 (Jun. 20, 2000).

Nitsch et al., "Serotonin 5-HT2a and 5-HT2c Receptors Stimulate Amyloid Precursor Protein Ectodomain Secretion," The Journal of Biological Chemistry 271(8): 4188-4194 (1996).

Morales, "Sideritis L." Flora Ibérica, vol. 12.

Öztürk et al., "Effects of Extracts from Certain Sideritis Species on Swimming Performance in Mice," Phytotherapy Research 10:70-73 (1996).

Pahnke et al., "Clinico-Pathologic Function of Cerebral ABC Transporters—Implications for the Pathogenesis of Alzheimer's Disease," Current Alzheimer Research, 5(4):396-405 (2008).

Pahnke et al., "Alzheimer's disease and blood-brain barrier function—Why have anti-β-amyloid therapies failed to prevent dementia progression?," Neurosci Biobehav Rev., 33(7):1099-1108 (Jul. 2009).

Pákáski et al., "Imipramine and citalopram facilitate amyloid precursor protein secretion in vitro," Neurochemistry International 47: 190-195 (2005).

Tunalier et al., "Antioxidant Properties and Phenolic Composition of Sideritis Species," Chemistry of Natural Compounds, 40(3):206-210 (2004).

"Aktualisierungsrecherche zum Bericht A05-19A (Cholinesterasehemmer bei Alzheimer Demenz) (Update search on report A05-19A (Cholinesterase inhibitors in Alzheimer's disease))," IQWiG Reports No. 67, produced by the IQWiG (German Institute for Quality and Efficiency in Health Care) (2009).

Search Report for corresponding European Patent Application No. 10174411.8, dated Jan. 25, 2011.

Search Report for related European Patent Application No. 11749166.2, dated Dec. 2, 2013.

Chow et al., "Potential cognitive enhancing and disease modification effects of SSRIs for Alzheimer's disease," Neuropsychiatric Disease and Treatment 3(5): 627-636 (2007).

Johne et al., "Interaktionen zwischen Phytopharmaka und anderen Arzneimitteln: Das Beispiel Johanniskraut (Interactions between herbal medicines and other drugs: The case for St. John's wort)," Bundesgesundheitsbl—Gesundheitsforsch—Gesundheitsschutz 46:1061-1067 (Dec. 2003) (see English abstract on p. 1062).

* cited by examiner

Sideritis dry extract according to Example 5 in an EEG animal model (n = 7)

Sideritis dry extract according to Example 5a in an EEG animal model (n = 7)

1200 mg of Sideritis dry extract according to Example 5 in a human experiment (n = 18, single administration)

Sideritis dry extract according to Example 5 in a water maze test (mice; n = 6)

Sideritis dry extract according to Example 5 in a water maze test (mice; n = 6)

Effects of Sideritis extract according to Example 12 in a water maze test – extended time test re-learning (mice; n = 6)

PLANT EXTRACTS MADE OF *SIDERITIS* AND USE THEREOF TO BOOST COGNITIVE PERFORMANCE

CROSS REFERENCE TO RELATED APPLICATIONS

This application is a continuation of co-pending U.S. patent application Ser. No. 13/818,655 filed on Feb. 22, 2013, which is a national stage filing of PCT Application No. PCT/EP2011/064687 filed on Aug. 26, 2011, which claims priority to European Patent Application No. 10174411.8 filed on Aug. 27, 2010, both of which are incorporated herein by reference.

BACKGROUND OF THE INVENTION

*Sideritis* (*Sideritis* L.) is a genus of plants belonging to the Lamiaceae family. This genus contains some 140 species, which may be subdivided into roughly 320 subspecies, ecotypes and cultivars. It is composed of annual or perennial herbaceous plants and small shrubs. Several species are used as tisanes and are sold as Greek mountain tea. The geographical area of the genus stretches from the Atlantic islands of Western Europe and North-West Africa (Macaronesia), to the Mediterranean region and Russia, Tibet and Western China. The centre of origin is in the west of the area [Ramón Morales: *Sideritis* L., In: *Flora Ibérica*, vol. 12].

The mountain tea is usually made from *Sideritis* species whose botanical classification is at times difficult. Depending on the region, they have widely different names and some of them only a local meaning. Just in Turkey there are 46 and in Spain 45 species of *Sideritis*, many of which are endemic. In addition to their species diversity, what they all have in common is that they belong to the Lamiaceae family and can easily be mistaken for sage. The rural population often pick *Sideritis* plants on the mountain slopes and dry them for their own use. The aromatic tea then frequently consists of several *Sideritis* species. It is brewed with boiling water, drunk either hot or cold and can be sweetened with sugar or honey. Drinking such teas is a part of everyday life in many Mediterranean countries; its healthy effect tends to be of minor importance. The medicinal effects have been known for a long time, however, and were described as long ago as two thousand years by the famous Greek physician *Dioscorides* (the first century AD). We can read in his pharmacopoeia, for example, that *Sideritis* plants used as a compress "have the power to close wounds and prevent inflammation". Traditional folk medicine in the countries around the Mediterranean has made advances since the days of *Dioscorides*. Today, *Sideritis* plants are mostly used as teas and not so often as essential oils. They have a wide spectrum of applications: for relaxation where there are disorders of the gastrointestinal tract or for their calming effect in cases of insomnia and restlessness. Today's phytotherapists use the anti-inflammatory and antibacterial action to support treatment of infections of the lower urinary tract or bladder. Cold teas can also be used for gargling to alleviate inflammations in the mouth (throat and gums) and to help them heal more quickly. And drunk hot, the teas traditionally serve to prevent coughs and colds and in particular to fight respiratory diseases. Like many other Lamiaceae from the Mediterranean region (sage, thyme) the *Sideritis* species are also rich in essential oils but free from stimulating caffeine. Most varieties contain monoterpenes, which are regarded as an important raw material for many naturopathic medicines with only slight side effects. Various scientific studies have provided evidence of the therapeutic effects of many essential oils of the *Sideritis* species in the last few decades (e.g. stress-reducing).

In their search for effective phyto-active ingredients, scientists from the Mediterranean area have also studied their indigenous plants. A long-term programme was initiated at the Gazi University in Ankara (Turkey) to study the *Sideritis* genus, for example. The scientists examined the methods used in folk medicine and were actually able to show that various species of *Sideritis* did in fact have an antibacterial, anti-oxidative, palliative and anti-inflammatory effect.

There is, however, no or at the most only sketchy documentation showing which defined species exhibits a specific pharmacological activity. It is especially with regard to the influence on the human central nervous system that there is no information available about which *Sideritis* species in which type of preparation is particularly advantageous.

Cognition is a term not used uniformly referring to people and other systems processing information. What is often meant by "cognition" is thinking in a broad sense. Even if many cognitive processes in humans are conscious, "cognition" and "consciousness" do not mean the same thing. Certain processes in humans can be unconscious and yet cognitive, for example, one instance of this being unconscious learning. The cognitive abilities of a human being include attention, memory, learning, creativity, planning, orientation, imagination, reasoning, introspection, will, belief and quite a few more. Cognitive abilities are studied by various disciplines, such as psychiatry, psychology, philosophy and the neurosciences.

Cognitive performance is thus a complex process which can be quantified on brain power with measurable parameters.

The ability to learn includes not only committing something to memory (duration and quantity of the input retained) but also the influence on the reaction speed, the ability to carry out logical operations (quickly and correctly), and spatial intellectual powers, such as during a period of orientation under new or changed conditions. Dysfunctions in this cognitive capacity are described with, inter alia, the syndrome MCI (Mild Cognitive Impairment). MCI constitutes a special condition of an age-related reduction in cognitive functions and abilities. This syndrome is not only characterised by the subjective loss of the powers of memory; other cognitive mechanisms are generally affected too (e.g. attention, executive functions). Testing healthy people for MCI can be regarded as a pre-indicator for later forms of dementia. The final stage of losing cognitive faculties then results in absolute disorientation, both spatially and with regard to time (e.g. Alzheimer's disease).

Electroencephalography (from Greek enkephalon 'brain', graphic 'writing') is a method used in medical diagnostics to measure the totalised electrical activity of the brain by recording the voltage fluctuations on the scalp. The electroencephalogram (abbreviated to EEG) provides a visual trace of these fluctuations and is a standard technique in neurology. The cause of these potential differences are physiological processes in individual brain cells which through changes in their electrical state affect how the brain processes information. According to their specific spatial arrangement, the potentials produced by individual neurons add up and changes in potential over the entire head can be measured. Recordings in at least twelve channels of different combinations of electrodes are needed for clinical evaluation. The spatial resolution of the usual EEG is several centimetres. If a higher resolution is needed, the skull first has to be opened up surgically and the electrodes then have to be placed directly on the cortex to be examined. This is only necessary in exceptional cases, however, for example before surgery for epilepsy. Such a procedure is known as an electrocorticogram (ECoG) and it enables a spatial resolution of less than 1 cm. In addition, it is then possible by means of selective electrical stimulation of one of the electrodes to test the function of the cortex lying underneath. Ascertaining single-cell activity in greater detail is only possible by carrying out tests on animals. The data acquired can be examined for unusual patterns by skilled specialists. A common mathematical method for analysing an EEG is the Fourier transformation of the data from the time domain (i.e. the usual way of showing changes in voltage over time) to the so-called frequency domain. The picture this produces enables rhythmic activity to be quickly determined. With the paperless or computer EEG, the signal is digitised and usually evaluated by the neurologist or psychiatrist on their screen.

The macroscopically visible electrical brain activity may exhibit motifs which closely resemble rhythmic activity. The EEG does resemble the frequency-dependent noise (pink or 1/f noise), however, and does not contain any long-lasting oscillations. Various levels of awareness are accompanied by changes in the frequency spectrum of the EEG signals. Vague statements on the state of consciousness can thus be made by analysing the voltage waveforms measured. The EEG is frequently divided into frequency bands (so-called EEG bands), although the number of bands and also their precise division are at times given differently. There are historical reasons for how the frequency bands are divided and their ranges; they are not all congruent with ranges which are regarded as appropriate on the basis of more recent studies. The theta band, for instance, has been divided into a theta 1 and theta 2 range to allow for the different meanings of the subranges. EEG evaluation is traditionally done by trained evaluators recognising patterns. It is especially for long-term and sleep EEGs that software algorithms designed to reproduce this pattern recognition are also used for assisted or automatic evaluation. This proves to be easier for the EEG bands defined mainly in the frequency range but it is somewhat more difficult for other typical patterns in the EEG. A highly asynchronous pattern of all frequency bands, for example, suggests strong emotional stress or loss of voluntary control while increasingly slow waves coupled with few fast waves indicate a state of sleep or dozing.

Delta waves have a low frequency of 1 to 4 Hz. They are typical for the dreamless, slow-wave sleep period (deep sleep). Delta waves are influenced by intervention in the cholinergic system.

A signal in the frequency range between 4 and 7 Hz is known as a theta wave. They occur with increasing frequency in the light stages of sleep and one only reacts to important or powerful stimuli from the environment. Theta waves are changed by interactions with the noradrenergic alpha-2 receptor.

A signal in the frequency range between 8 and 13 Hz is known as an alpha wave. An increase in the number of alpha waves is associated with light relaxation or relaxed wakefulness with the eyes closed. Alpha waves mainly appear when the eyes are closed and then change to the beta range when the eyes are opened. The same effect can be achieved with the eyes closed if a person begins to solve a simple arithmetical problem in his head, for example. A distinction is made between alpha-1 and alpha-2 waves. Alpha-1 waves appear to be under serotonergic control; alpha-2 waves change with changes in the activity of the dopaminergic system.

Beta waves occupy a range between 14 and 30 Hz. There are various meanings attached to the occurrence of beta waves and reasons for them; beta waves are found in some 8% of all people, for instance, as normal EEG variants. Beta waves also appear in REM sleep. β-oscillations also occur physiologically when holding a constant force, for example. A signal in the frequency range above 30 Hz is known as a gamma wave. Hard concentration causes them to appear, for example, or learning processes. More recent research has shown the significance of the gamma range with regard to the so-called top-down regulation and synchronisation of various areas of the brain for integrating different qualities of a stimulus. A distinction is made in an EEG between changes primarily in the beta-1 and beta-2 waves. Changes in the beta-1 waves can be observed when there are interventions in the glutamatergic system. Drugs which intervene in the GABA-ergic system produce changes in the beta-2 waves.

But brain waves can not only be measured; they can also be influenced. This may take place by stimulating sensory nerves (visual, acoustic or olfactory stimuli) or as neurofeedback—a special form of bio-feedback—as a result of pharmacologically active substances, such as psychotropic drugs [Dimpfel W, et al. (1996) Source Density Analysis of Functional Topographical EEG: Monitoring of Cognitive Drug Action. Eur J Med Res 1: 283-290]. The evaluation is also referred to as an electropharmacogram. With neurofeedback it is usual to subdivide the EEG bands more finely and to interpret them differently to the clinical EEG. An increased amplitude within the frequency ranges is correlated with certain mental states or activities. Theta-2 waves can be associated with recollection and learning ability, concentration and/or creativity, for example. After extensive calibrations, conclusions can likewise be drawn about neurotransmitter-communicated CNS activities, which can be divided into dopaminergic, serotonergic, cholinergic or noradrenergic subgroups.

SUMMARY OF THE INVENTION

The aim of this invention is to provide additional uses of preparations and extracts of the *Sideritis* genus (*Sideritis* ssp.).

The task is solved by the use as described in the invention of preparations and extracts of the genus *Sideritis* (*Sideritis* ssp.) to boost cognitive performance, in particular the use of selected *Sideritis* species and/or their combination to produce aqueous or hydroalcoholic extracts. These extracts can be used in foodstuffs, nutritional supplements, supplementary balanced diets or pharmaceutical preparations.

Öztürk, Y. and Aydin S. (Phytotherapy Research, vol. 10, 70-73 (1996)) describe a sedating activity for preparations of various *Sideritis* species, which they derive from the "Swimming performance test". This is normally a measure for the motivation ability in depressive mice, however, or an endurance test for measuring the effects of muscle-strengthening foodstuffs. Influences on cognitive skills were not described.

Serotonergic neurotransmission being influenced is described for plants of the genus *Sideritis* in the patent application EP 1 634 602. This document unfortunately revealed no details whatsoever on the species used, however; nor was there any information on any influence on the selection of the extraction medium may have had. The experimental set-up described in paragraphs [0046] to

[0054] for measuring serotonergic re-uptake rates was used for initial screening of suitable species for the tests.

The invention describes producing plant extracts from *Sideritis* ssp. and their use in boosting cognitive performance.

According to the animal model "Morris water maze" (also known as the "Morris water navigation task"), the increase in cognitive performance becomes particularly evident in a situation creating strain in which an increase in the learning performance and especially in retentiveness has been demonstrated.

The situation creating strain in this case was produced by a stress situation but it could also have been triggered by a neurodegenerative disease. In tests on human beings the strain situation was triggered by learning stress, in particular in conjunction with new tasks in a special situation, e.g. suffering from examination nerves.

The tests carried out show that it is in particular aerial plant parts of plants from the group *Sideritis euboa, Sideritis scardica, Sideritis raiseri* and *Sideritis pisidica* which are suitable, irrespective of the degree of drying of the drug. Drying below 12% proves to be especially advantageous with regard to the storage life of the drug as it minimises the process of decomposition and keeps the microbiological contamination of the drug at low levels. Extraction is assisted and active ingredient yields improved if sizes are reduced to 1 cm, especially if the proportion of stems is reduced after destemming and airstream sorting.

*Sideritis* develops its strongest aroma when it is in bloom. For use in a foodstuff, the best time for harvesting the drug has therefore proved to be this stage of its growth.

If a mixture of several subspecies is to be used, it is best to have a large proportion of *S. scardica*; this should preferably be an *S. scardica* proportion of no less than a half, ideally at least 80%, however.

Based on experience from solvent screening, it is in particular polar extractants such as water, monovalent and polyvalent alcohols or ketones which are suitable for the extraction process, especially alcohols or ketones having 1 to 4 C atoms and in particular their mixtures with water. Without giving a definitive list, the following extractants may be regarded as particularly suitable: methanol, ethanol, 1-propanol, 2-propanol, propane-1,2-diol, propane-1,3-diol, glycerol, acetone and methyl ethyl ketone. Using sugars (monomers, dimers and oligomers) as well as low-molecular polyethylene glycols as cosolvents is also conceivable.

Extraction is best carried out at temperatures no greater than 10° C. below the boiling point of the extractant so as to keep the system pressure as low as possible. Additionally, the best temperature for the aromas has been shown to be no higher than 100° C. In order that the extractants may flow with the lowest possible pressure, a flow temperature of at least room temperature, i.e. about 20° C., has proved to be the most suitable.

In order to facilitate handling the extracts on a large scale, the extraction eluate is ideally enriched to over 50% dry matter content by removing the solvent. Methods which are particularly gentle and energy-efficient for this are ones using vacuums at moderate temperatures of approximately 50° C.

Handling capabilities and storage stability are yet further improved by drying them to the greatest possible extent. Today's state of the art usually sees this being done with the aid of freeze drying, spray drying, belt drying, vacuum drying, drum drying or a combination of these techniques.

The use of the extracts produced in this way is conceivable in foodstuffs, nutritional supplements, supplementary balanced diets or pharmaceutical preparations (medicines).

The extract would then usually be converted into a form suitable for the user, such as a tablet, a capsule, a form which can be chewed or sucked, an effervescent tablet or powder, a granulate, a beverage or an instant mixture, especially an instant tea mixture.

Physiologically well-tolerated additives are commonly used to obtain the dosage required in such a form. These include carbohydrates such as starch breakdown products, e.g. maltodextrin, glucose syrup and sugar, but also cellulose and the corresponding carbohydrate derivatives. In addition, gum Arabic, gelatin and collagen hydrolysates from the group of the proteins are also used.

If use is to be for therapeutic purposes, a synergistically acting combination with nootropics would also be possible; this is also used in treatment for dementia, for example. Potential combination partners would be acetylcholinesterase inhibitors (e.g. donepezil, galantamine, rivastigmine, tacrine and their derivatives), GABA analogues (e.g. piracetam and derivatives), ergot derivatives (e.g. nicergoline, dihydroergotoxine and derivatives) and NMDA antagonists (memantine).

A method comprising the following steps has proved to be particularly suitable for producing an extract from *Sideritis* ssp:

a) from the species *Sideritis euboa, Sideritis scardica, Sideritis raiseri, Sideritis pisidica* or their mixtures, the aerial plant parts are selected b) and harvested when they are in bloom, c) optionally dried to a residual moisture content of <12%, d) optionally cut to approx. 1 cm, airstream sorting and as many of the stems separated as possible, e) extraction carried out with an extractant selected from the group water, monovalent and polyvalent alcohols or ketones, especially alcohols or ketones having 1 to 4 C atoms or their mixtures, extraction being at f) an extractant temperature between 20 and 100° C., preferably at temperatures 10° C. below the boiling point of the extractant, g) at least some of the extractant is removed, preferably gently by means of a vacuum, h) the essential oil depleted in a vacuum to less than 0.1% in the extract, i) the resultant extract is dried, preferably with freeze drying, spray drying, belt drying, vacuum drying, drum drying or a combination of these techniques.

BRIEF DESCRIPTION OF THE DRAWINGS

FIG. 2 shows the effect of the *Sideritis* dry extract as in example 5a.

Figure 1:
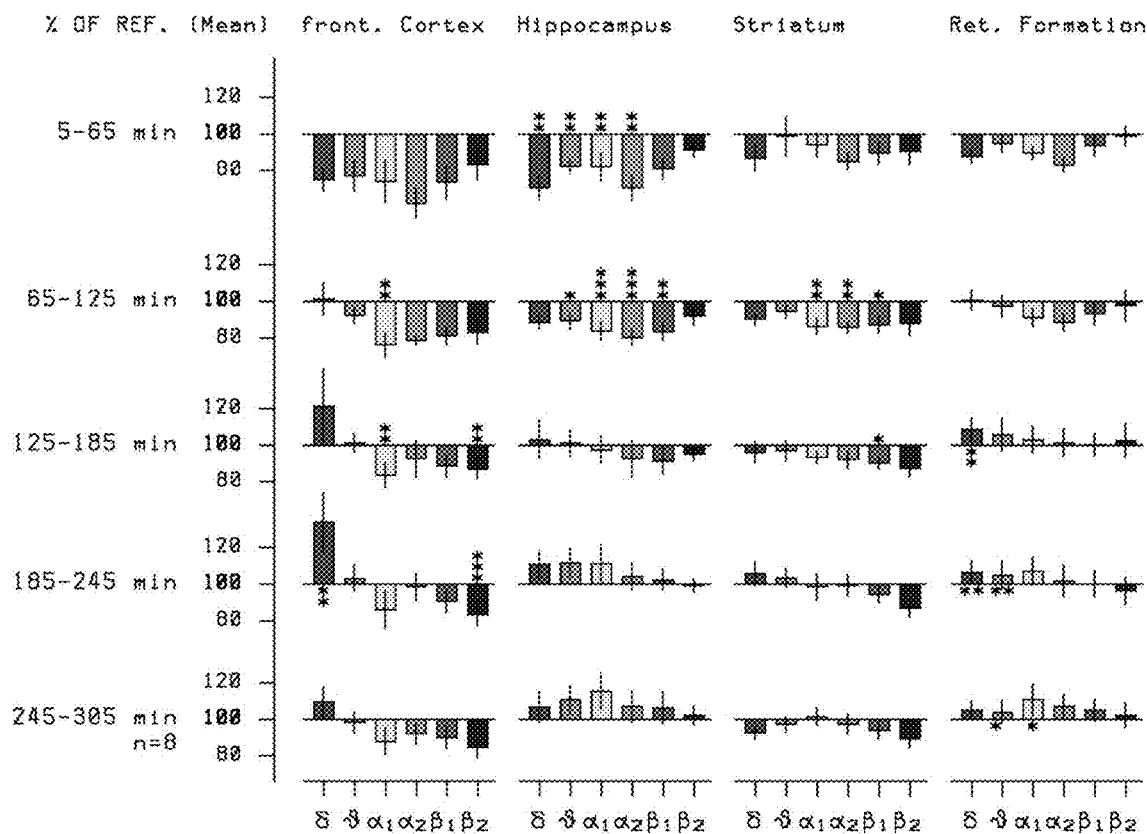
FIG. 1 shows the effect of the *Sideritis* dry extract as in example 5 in the EEG animal model; cf. example 7.

The following examples explain the invention in greater detail:

DETAILED DESCRIPTION OF THE INVENTION

Example 1

Producing Tea-Like Extracts from the Herb *Sideritis*

50 g of the herbal drug is mixed twice with 15 times the quantity of boiling water and extracted with agitation. Both maceration extracts are allowed to stand at room temperature to cool down and combined. The two combined macerations are filtered off with a fluted filter and concentrated to a soft extract using a rotary evaporator. The extractive yields determined for the different species are shown below. In order to test for the serotonin absorption inhibition, the extracts were all weighed in at the same native content and assayed with a measuring concentration of 50 μg/ml in the test system according to EP 1 634 602.

A negative control with serotonin shows 0%; a positive control with (10 μm) of the reference substance fluvoxamine 100%.

| Species | Extractive Yield [%] | Serotonin Absorption Inhibition [rel. % vs. control] |
|---|---|---|
| Sideritis congesta | 22.8 | 5 |
| Sideritis vuralii | 25.9 | 10 |
| Sideritis argyrea | 25.3 | 12 |
| Sideritis arguta | 17.0 | 17 |
| Sideritis pisidica | 19.3 | 12 |
| Sideritis scardica | 15.7 | 39 |
| Sideritis raiseri | 17.1 | 31 |
| Sideritis euboa | 17.2 | 28 |

In keeping with the habitus of the individual species (different stems and quantities of leaves), the yields vary between approx. 16-26%, with high extract yields, such as with *Sideritis vuralii*, accompanied by a low activity. The species *S. scardica*, *S. raiseri* and *S. euboa* with a relatively low yield are favoured vis-à-vis serotonin absorption inhibition.

Example 2

Producing Inventive Hydroalcoholic Extracts from the Herb *Sideritis*

50 g of the herb *Sideritis* was mixed twice at 45° C. with 15 times the quantity of a mixture of water and ethanol and extracted with agitation. Both maceration extracts were allowed to stand at room temperature to cool down and combined. The two combined macerations were filtered off with a fluted filter and concentrated to a soft extract using a rotary evaporator. The extractive yields determined for the different species are shown below. In order to test for the serotonin absorption inhibition, the extracts were all weighed in at the same native content and assayed with a measuring concentration of 50 μg/ml in the test system according to EP 1 634 602.

A negative control with serotonin shows 0%; a positive control with (10 μm) of the reference substance fluvoxamine 100%.

| Species | Extractant + Concentration | Serotonin Absorption Inhibition [rel. % vs. control] |
|---|---|---|
| Sideritis euboa | 20% v/v ethanol | 58 |
| Sideritis scardica | 20% v/v ethanol | 65 |
| Sideritis pisidica | 20% v/v ethanol | 28 |
| Sideritis pisidica | 30% v/v ethanol | 64 |
| Sideritis pisidica | 50% v/v ethanol | 25 |
| Sideritis pisidica | 70% v/v ethanol | 19 |

The influence of the extractant was assayed using the species *S. pisidica*. Increasing the ethanol content to 20% v/v compared with pure water results in activity 2.3 times stronger. Just a 10% v/v increase in extractant strength of ethanol 30% v/v produced activity 5.3 times higher. Further increases in ethanol did not result in any more rises; in fact a significant drop can actually be measured for ethanol 50% v/v and ethanol 70% v/v. A concentration of 20-30% v/v ethanol is a preferable extraction strength. This also becomes evident from the favoured species under example 1, where increased activity by the factor 1.7 for *S. scardica* and by the factor 2.0 for *Sideritis euboa* can be demonstrated.

Example 3

Producing an Inventive Hydroalcoholic Extract from a Fresh Plant 100 g fresh drug from the herb *Sideritis scardica* was mixed twice at 45° C. with 15 times the quantity (v/v) 20% ethanol and percolated. Both percolates were allowed to stand at room temperature to cool down, filtered off with a fluted filter and concentrated to a soft extract using a rotary evaporator.

This produced the following serotonin absorption inhibition at a measuring concentration of 50 μg/ml in the test system according to EP 1 634 602:

| Species | Extractant + Concentration | Serotonin Absorption Inhibition [rel. % vs. control] |
|---|---|---|
| Sideritis scardica fresh plant | 20% v/v ethanol | 45 |

Example 4

Producing an Inventive Hydroalcoholic Extract from Dried, Pretreated *Sideritis* Raw Material The herb *Sideritis scardica* was harvested fresh and dried whole within 7 days by means of heated circulating air. The residual moisture content was 10.2%.

The product obtained is packaged and used for making tea.

To ensure use for extraction, a cut herb product 2-5 cm long is generally used. Optimisation of the extractive content is expected of cut products (1 cm). Destemming the *Sideritis* herb produces a special embodiment. Machines are used in this process to separate the leaves and flowers from the stems. Airstream sorting can then reduce the proportion of stems to less than 5%.

The three differently processed raw materials of *Sideritis scardica* were extracted with (v/v) 20% ethanol using the method described in example 2. This produced the following serotonin absorption inhibition at a measuring concentration of 50 μg/ml in the test system according to EP 1 634 602:

| Sideritis scardica dried raw material | Extractant Yield [%] | Serotonin Absorption Inhibition [rel. % vs. control] |
|---|---|---|
| 6-8 cm | 16.2 | 65 |
| 1 cm normal stem content | 17.5 | 64 |
| 1 cm reduced stem content | 21.3 | 64 |

The test shows that pretreating the raw material increased the yield by a relative 31%, while the pharmacological activity remained unchanged.

Example 5

Producing a Sideritis Extract Preparation a) 10 kg of the herb Sideritis scardica L. underwent extraction in a percolator at 45° C. for 8 hours in a batch with 300 litres (v/v) 20% ethanol and the drug removed by means of a 250 μm filtration bag. The eluate was left to cool down at room temperature and clarified using a cellulose filter. It was then concentrated in a vacuum to a soft extract with a dry substance content of approx. 50%. The extract yield was 16%, which is equivalent to a native drug extract ratio of 6:1. 30% maltodextrin as the carrier was added to 70% native extract for the drying batch and dried in a vacuum at 50° C.

b) 10 kg of the herb Sideritis euboa L. underwent extraction in a percolator at 45° C. for 8 hours in a batch with 300 litres (v/v) 20% ethanol and the drug removed by means of a 250 μm filtration bag. The eluate was left to cool down at room temperature and clarified using a cellulose filter. It was then concentrated in a vacuum to a soft extract with a dry substance content of approx. 50%. The extract yield was 17%, which is equivalent to a native drug extract ratio of 6:1. 30% maltodextrin as the carrier was added to 70% native extract for the drying batch and dried in a vacuum at 50° C.

The two dry extracts a) and b) obtained were each ground to a homogeneous extract powder with the aid of a 1 mm screen. The mixture of a Sideritis scardica dry extract (a) with a Sideritis euboa dry extract (b) in a ratio of 1:1 produces a preparation according to the invention.

Example 6

Producing a Sideritis Extract Preparation 10 kg of the herb Sideritis scardica L. underwent extraction in a percolator at 80° C. for 8 hours in a batch with 300 litres (v/v) water and the drug removed by means of a 250 μm filtration bag. The eluate was left to cool down at room temperature and clarified using a cellulose filter. It was then concentrated in a vacuum to a soft extract with a dry substance content of approx. 50%. The extract yield was 17.5%, which is equivalent to a native drug extract ratio of 6:1. 30% maltodextrin as the carrier was added to 70% native extract for the drying batch and dried in a vacuum at 50° C.

Example 7

Telestereo EEG Measurement on Freely Moving Rats-1 with the Preparation Described Under Example 5

4 semimicro electrodes were implanted into the 4 brain areas "frontal cortex", "hippocampus", "striatum" and "reticular formation" of a group of n=8 Fischer 344 rats. The measurable potential field changes were transmitted wirelessly and evaluated to produce an electropharmacogram. The animals were exposed to Sideritis dry extract mixture (from example 5) in three different dosing equivalents (50, 100, 200 mg/kg b.w. oral) in a cross-over design. Each individual dose was dissolved in water and administered once after one week "wash-out". A normal saline solution served as a control experiment. After a 45-minute, pre-drug observation period, the test liquid was fed by gavage and there followed a 5-minute period of calming down for the animal. Measuring for a period of 5 hours then commenced. The frequency data were obtained using Fast Fourier Transformation (FFT) and the mean taken in 60-minute periods. Statistical evaluation was by means of the Wilcoxon, Mann and Whitney U test against the control (saline solution).

All dosages produced comparable frequency patterns. The greatest effects could be seen with the alpha-2 waves, which denote dopaminergic neurotransmission. Even with a dosage of 50 mg/kg b.w. it was also possible to significantly differentiate the beta-1 waves belonging to the glutaminergic system from the control. The delta, theta and—especially from higher measuring concentrations—the alpha-1 waves too were also attenuated, which is in keeping with the activation of cholinergic, noradrenergic and serotonergic neurotransmission.

See FIG. 1 for the results.

Example 8

Telestereo EEG Measurement on Freely Moving Rats-2 with Sideritis scardica Dry Extract from Example 5a The measuring model was used in the same way as the test set-up described in example 7 to measure the influence on the electropharmacogram with the Sideritis scardica dry extract from example 5a prior to mixing. The same dosing was chosen (50, 100, 200 mg/kg b.w. oral). Each dose was again dissolved in water and administered once after one week "wash-out". A normal saline solution likewise served as a control experiment.

All dosages produced comparable frequency patterns in the frontal cortex, which is particularly significant for learning ability. The greatest effects could again be seen with the alpha-2 waves, which denote dopaminergic neurotransmission. It was also possible to clearly differentiate the beta-1 waves belonging to the glutaminergic system from the control.

Figure 2:
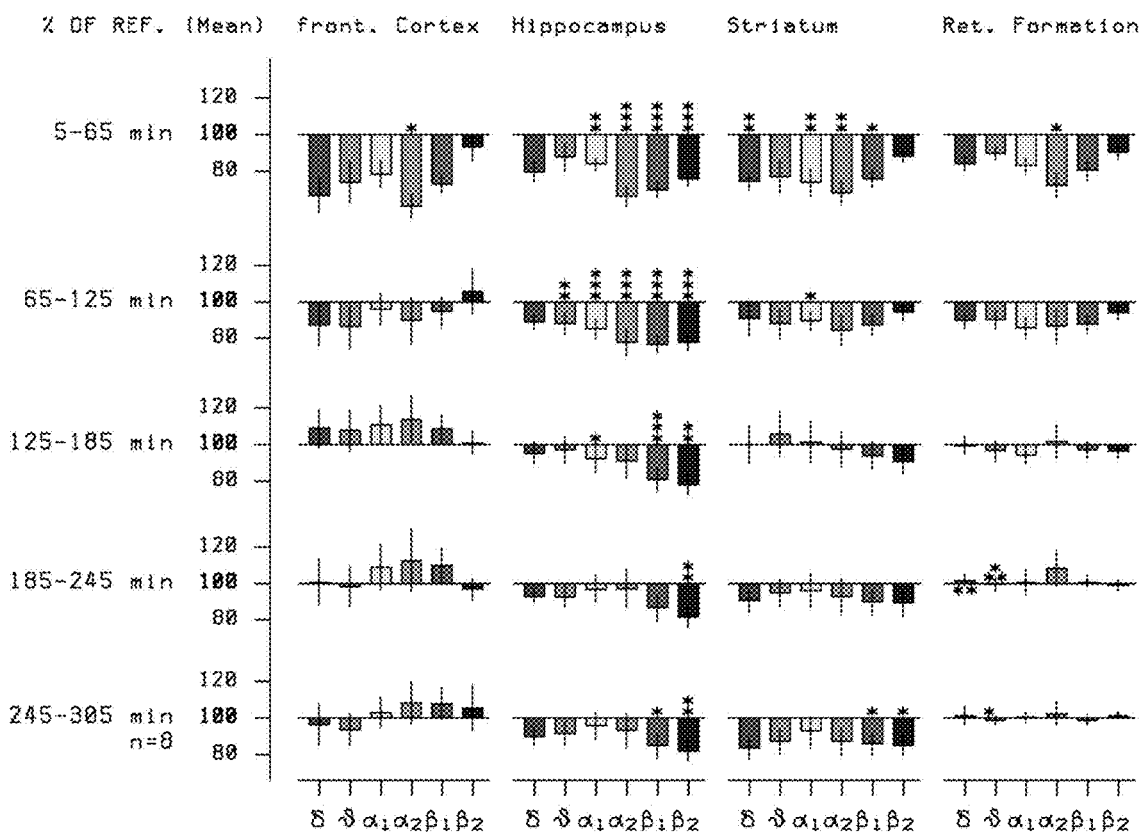

See FIG. 2 for the results

Example 9

EEG Measuring in a Double-Blind, Randomised, Placebo-Controlled Human Study in Cross-Over Design for Evaluating a Single Dose Capsules each containing 400 mg were filled from the test mixture (example 5), of which 3 capsules in each case form a single dose in the study.

The study was carried out to detect any increase in performance in the cognitive area after acute ingestion of a Sideritis extract. To this end, test persons with a mild cognitive impairment were recruited with the help of an interactive question test (DemTect Score 9-13) [Kessler J, et al. (2000) DemTect. Ein neues Screening-Verfahren zur Unterstützung der Demenzdiagnostik (*DemTect. a new*

*screening test to support the diagnosis of dementia*). Psycho 26: 343-7]. A group of n=18 otherwise healthy subjects aged between 40 and 65 were classified accordingly and then tested for the effects of the extract as described in example 5.

Figure 3:
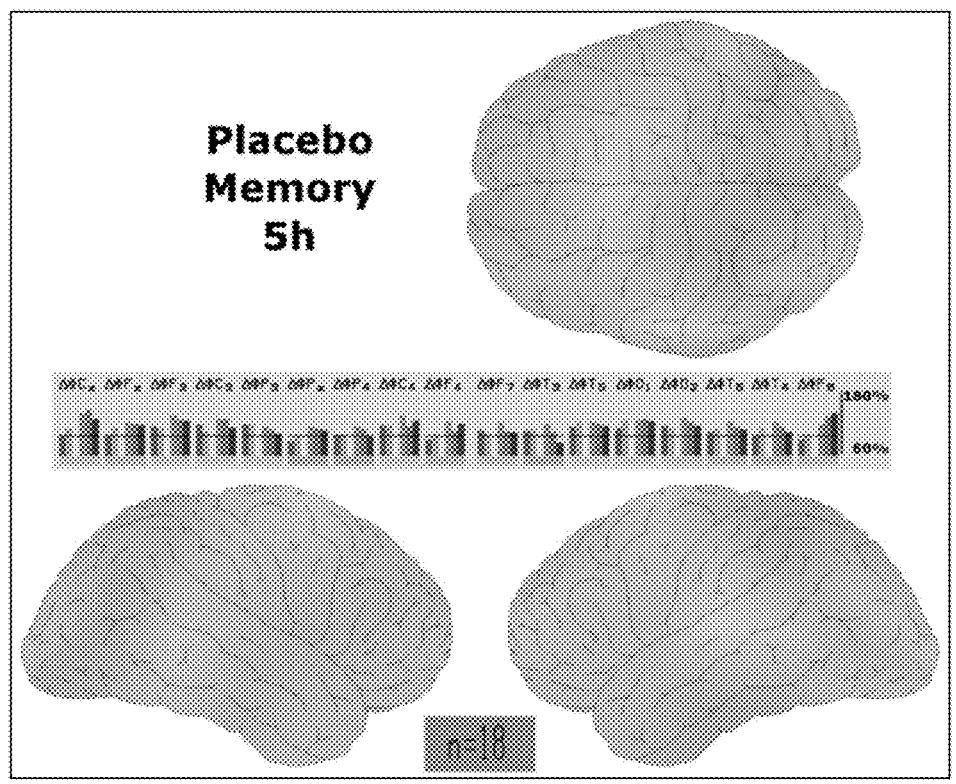
FIG. 3 shows a "brain map" after administering *Sideritis* dry extract; cf. example 9.
Figure 3:
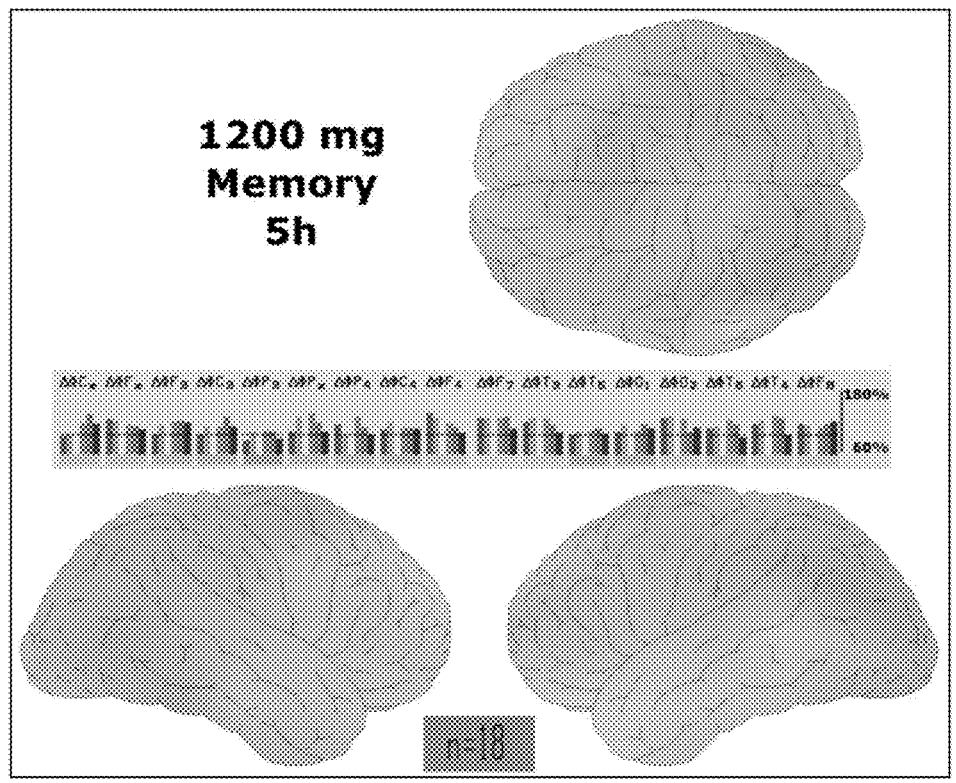

The electroencephalogram of the test subjects was derived under relaxed conditions and while carrying out three different cognitive tests (electropsychogram). Changes in electrical activity compared with taking a placebo were measured both in the relaxed state and when carrying out the memory test. In the relaxed state there was a drop in the alpha waves (significant for alpha-2 waves in the last hour with p<0.07). Changes in comparison with the placebo are shown in FIG. 3 as a "brain map". An increase in the slow delta and theta waves was observed while carrying out the memory test, while there was a decrease in the faster alpha and beta waves. Statistically significant were the increase in the alpha-1 waves (5th hour after ingestion; p<0.02) and the decrease in the beta-2 waves (1st hour after ingestion; p<0.07). An increase in the frontal slow waves also became noticeable in the brain map. An increase in the slow waves with a simultaneous decrease in the fast waves is characteristic for mental work.

The results of the neurophysiological data analysis provide an initial indication of a stimulating effect of the extract (suppression of the central alpha-2 activity) with changes in the electrical activity while carrying out the memory test, which may be interpreted as improved performance (increase in the frontal delta and theta waves, greater decrease in the central alpha-2 and beta-1 waves). An increase in memory performance can thus be detected after a single ingestion. The extract was very well tolerated and there were no side effects.

Example 10

Case Example—Drinking Tea and EEG Measurement

The consumption of approximately 500 ml of a cooled *Sideritis scardica* tea was monitored by means of EEG in a self-experiment of a 42-year-old man. It showed that both the alpha-2 waves were attenuated and the delta and theta waves were excited. There was a significant improvement in the memory test carried out after consumption and also in the powers of concentration.

Example 11

Behaviour Tests in the Morris Water Maze (MWM)

Test animals, in this case mice, are trained over a period of several days in a round pool filled with cloudy water and with visual cues (conspicuous markers) placed around the pool, to find on their own an invisible platform hidden below the surface of the water and to remember its spatial location. The mice are placed into the water at a distance of approximately 30 cm from the edge, whereupon they try to reach the escape platform with swimming movements. This measuring system has been known since the 1980s and its advantage over conventional simple mazes is that there are no local landmarks but only global ones and that there is a high motivation factor involved in the task because the animals want to escape. The primary aim of the experiment is to test the (spatial) learning (recognition and memory) of the animals under conditions of stress and to measure the potential influences on this. The parameters recorded are the time it takes to locate the platform, the distance covered up to that point and the relative time spent in the right quadrant of the pool. These parameters are influenced by the training effect: there is usually a reduction in the time taken to locate the platform and in the distance covered, for example, while the time spent in the quadrant increases. Moreover, the training effect can be influenced by different neurotransmitter concentrations [dissertation, Freiburg University 2004, Theresa Schweizer: 3,4-Diaminopyridin evozierte Freisetzung von Neurotransmittern aus Hirnschnitten von Ratten/3,4-diaminopyridine evoked release of neurotransmitters of brain slices of the rat: Untersuchungen im Kortex und Hippocampus an alten Ratten, sowie an Ratten mit serotonergen Läsionen hippocampaler Afferenzen und intrahippocampalen Raphé-Transplantaten].

4 groups of 6 mice each were tested in this experimental set-up. The first control group consisted of transgenic animals treated with water (strain APPS1+/0) which on account of their genetic disposition manifest a high level of β-amyloid deposition within 50 days of their birth and develop Alzheimer's disease. The second control group was formed by healthy reference mice (control strain APPPS1 0/0) without the particular gene mutation. The third group was composed of transgenic animals (strain APPS1+/0) which received by gavage a *Sideritis* extract solution from example 5 from the fiftieth day of their life. The fourth group was formed by transgenic animals (strain APPS1+/0) which were treated (fed by gavage) with an extract solution of *Ginkgo biloba* (produced according to the European Pharmacopoeia) of the same concentration from the fiftieth day of their life. This group was selected because *Ginkgo biloba* extracts are the most used medication in such cases.

Testing based on behavioural biology commences at the age of approx. 95 days using the Morris Water Maze (95-100 d). The test comprises a daily early and late test/learning unit over four days. The early unit begins with a run without a platform for 30 seconds and the time is recorded of how long the mouse spends in the quadrant in which the platform is usually located (target quadrant). The other four runs are with an invisible platform and 4 different starting positions.

Two parameters were analysed: the time taken to reach the platform (escape latency, FIGS. 4 and 5) and the time which the mice spent in the target quadrant in the first run of the last day.

Figure 4:
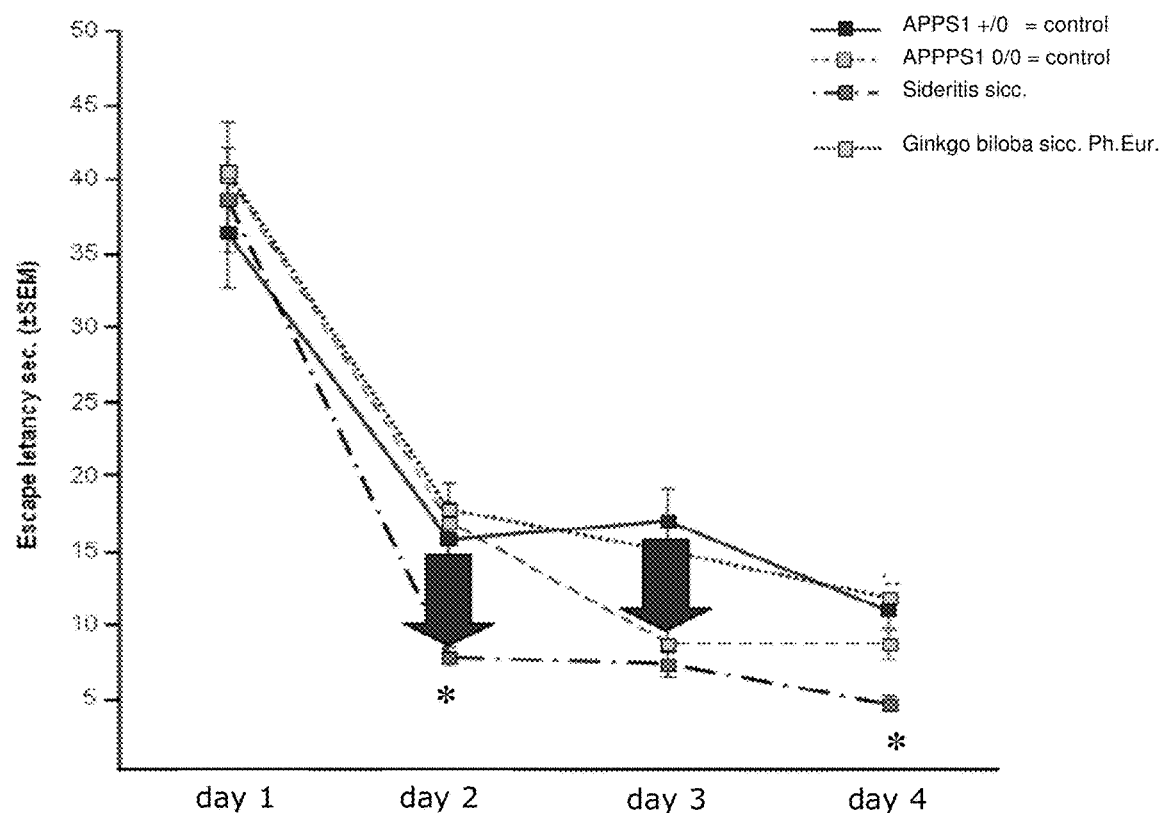
FIG. 4 shows the results in the Water Maze Test as in example 11.
Figure 5:
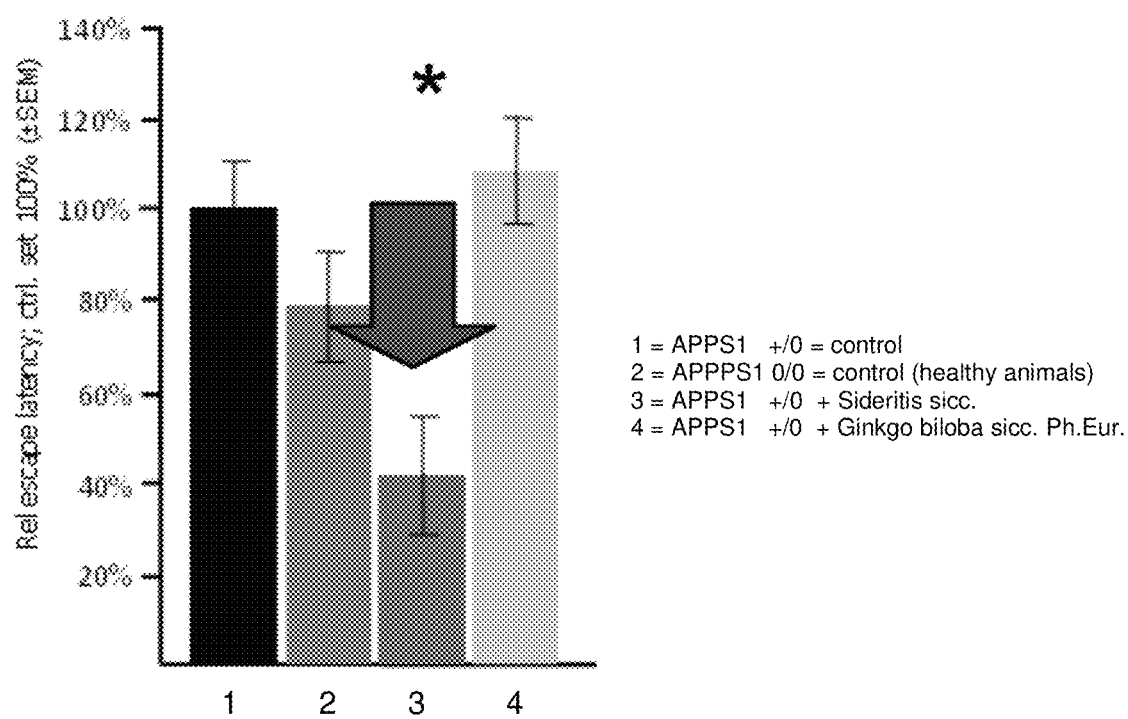
FIG. 5 summarises the results from example 11.

Both parameters show that the *Ginkgo* extract (FIG. 4=dotted line, FIG. 5=no. 4) compared with the transgenic control (FIG. 4=continuous line, FIG. 5=no. 1) does not have any influence on the cognitive performance in this mouse model. By way of contrast, treatment with *Sideritis* extract mixture produces an impressive increase in memory performance. Animals treated with *Sideritis* extract (from example 5; FIG. 4=broken line, FIG. 5=no. 3), for instance, are significantly faster in reaching the platform as early as on day 2 and also on days 3 and 4. Even when compared with the "healthy animals", the treatment resulted in a considerable increase in the learning performance on days 2 and 4.

Example 12

Behavioural Tests (Healthy Mice) in the MWM

Testing based on behavioural biology commences at the age of approx. 95 days in the Morris Water Maze test model as described in example 11 (95-100 d). n=6 animals in accordance with the second control group (control strain APPPS1 0/0) are compared with a parallel test group n=6 (strain APPPS1 0/0) which have been treated with a *Sideritis* extract (from example 5) from the fiftieth day of their life. Both the escape latency and the time spent in the target quadrant showed an impressive increase in memory performance on days 2, 3 and 4.

After roughly a further 35 days the test set-up was again used to compare both test populations (d135-d150). The *verum* population was treated again for 15 days with (12 g/kg b.w.) *Sideritis* extract (example 5). The result was an escape latency of the *verum* population reduced by 53% on day 4 as well as an increase in the period of time spent in the target quadrant by over 30%.

This test procedure was repeated after another 150 days (d275-d300), the *verum* population having been treated for 25 days beforehand with 6 g/kg b.w. *Sideritis* extract (example 5). Even after this long period of time, a significant decrease in the escape latency by 40% was nevertheless observed on day 1.

Tests were subsequently carried out on both populations to see if a new learning process could benefit from taking the *Sideritis* extract for a short time. This saw the platform relocated to a different quadrant. There was thus no measurable difference in the escape latency on day 1 but already from day 2 the *verum* population was ahead and by day 4 it had increased its lead to 47%.

This process of new learning was tested once again at the age of d435-d450 (equivalent to a human age of roughly 90 years old). The *verum* population was again treated beforehand for 15 days with 6 g/kg b.w. *Sideritis* extract (example 5). Here as well, a reduction in the escape latency by 34% was observed first of all in the original target quadrant and then also on day 4 by 41% in the new target quadrant after it had been moved.

Figure 6:
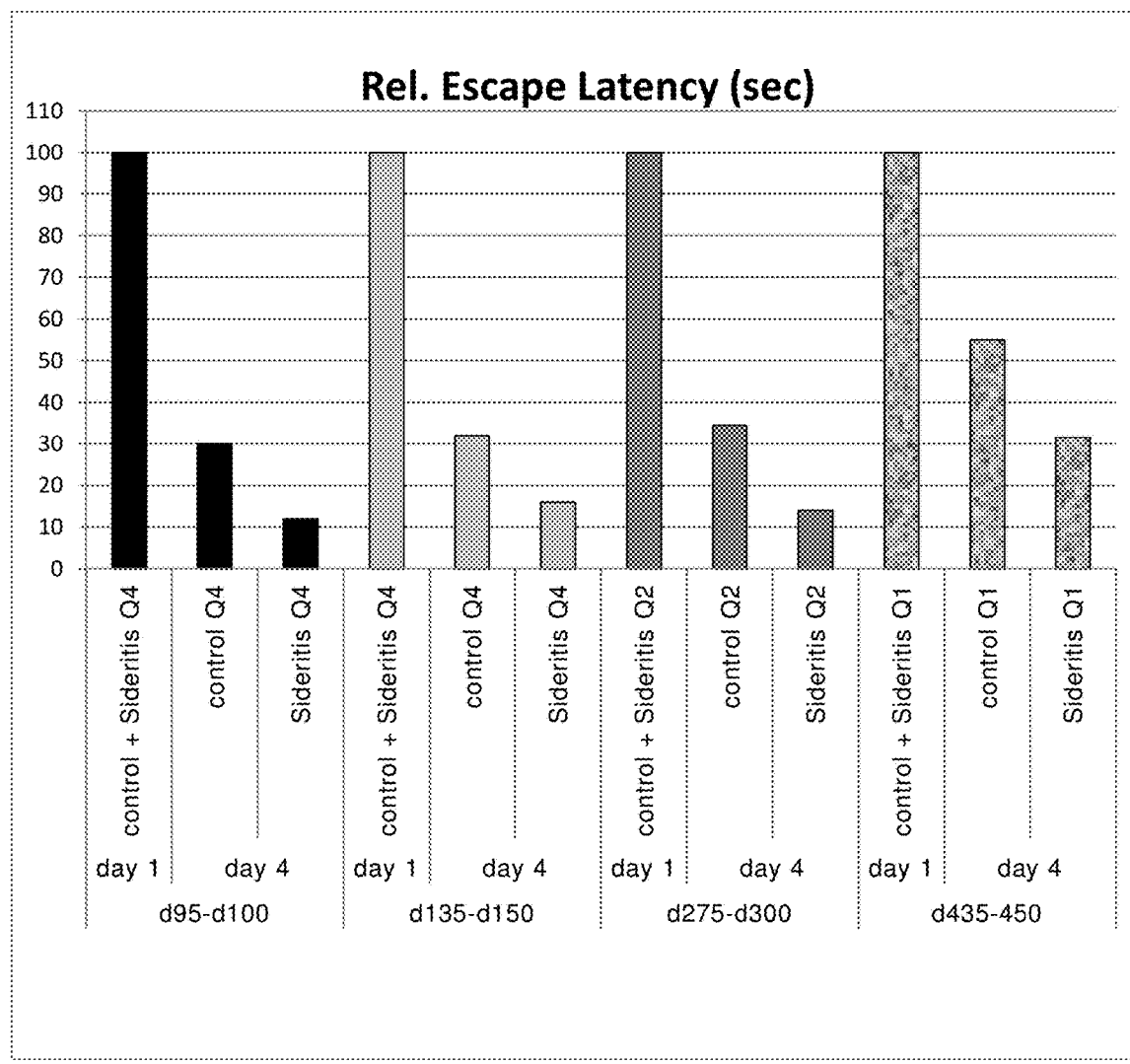
FIG. 6 shows the effect of *Sideritis* extract as in example 12.

The results are shown in FIG. 6.

Example 13

School Tea

Since it has its own aromatic taste, *Sideritis scardica* can be marketed as an aqueous tea extract in a slightly sweetened form as "school tea" in a classic tetrapack. The dry extract equivalent should be between 0.2 g and 2 g per 100 ml tea beverage. Suitable sweeteners are traditional sugars like fructose, glucose and sucrose, but also artificial sweeteners such as sodium saccharin, aspartame, sucralose, stevioside or the like. Increases in cognitive powers can be expected shortly after consumption because as seen in examples 9 and 10, the wave patterns are influenced in the EEG.

A typical composition for school tea is:

2.5 g *Sideritis scardica* extract as in example 6

0.8 g fructose

Water to 200 ml

Example 14

Instant Tea 2 kg of a soft extract of *Sideritis scardica* made according to the method described in example 6 is mixed with flavouring agents (250 g glucose, 10 g vitamin C, 1 g *Sideritis* liquid aroma, 0.8 g sucralose) and homogenised. The mixture is then spray-dried at an air intake temperature of 180° C. One measuring scoop of this powder can be dissolved in 150 ml cold water and can then be immediately drunk.

Example 15

Effervescent Formulation in a Sachet

To make effervescent tablets, 550 g citric acid is mixed with 300 g sodium bicarbonate, 50 g fructose and 100 g of the inventive extract produced from *Sideritis scardica* as described in example 6. After it has been homogenised, the mixture can be granulated or pressed straight into tablets. The recommended single dose is 4 g of the granulate or a 4 g effervescent tablet twice a day as required (=2×400 mg extract).

The invention claimed is:

1. A method for enhancing cognitive ability in a patient consisting essentially of identifying a desire to boost cognitive ability, administering therapeutically effective amounts of an extract from aerial plant parts of *Sideritis* ssp to the patient to enhance cognitive ability in the patient, wherein said aerial plant parts are selected from the group of *Sideritis euboa, Sideritis scardica, Sideritis raiseri*, or mixtures thereof, wherein the extract has been prepared by means of an extractant comprising a mixture of water and ethanol.

2. The method according to claim 1, wherein said enhancement of cognitive ability is enhancement of learning performance or enhancement of memory.

3. The method according to claim 2, wherein administering therapeutically effective amounts of an extract from aerial plant parts of *Sideritis* ssp is performed during an existing stress situation.

4. The method according to claim 3, wherein said existing stress situation is exam stress or neurodegenerative diseases.

5. The method according to claim 1, wherein the proportion from *Sideritis scardica* in the extract being at least 50%.

6. The method according to claim 1, wherein said aerial plant parts were harvested at the time of flowering.

7. The method according to claim 1, wherein said extract has been prepared with an extractant temperature of from 20 to 100° C.

8. The method according to claim 7, wherein said extract has been prepared with an extractant temperature 10° C. below the boiling temperature of the extractant.

9. The method according to claim 1, wherein said extractant has been removed at least partially.

10. The method according to claim 9, wherein said extractant has been removed by means of reduced pressure.

11. The method according to claim 9, wherein said extract has been dried.

12. The method according to claim 11, wherein said extract has been dried by freeze-drying, spray drying, belt conveyor drying, vacuum drying, roller drying, or a combination thereof.

13. The method according to claim 1, wherein said extract is contained in a food, a food supplement, a supplementing balanced diet, or a pharmaceutical formulation.

14. The method according to claim 13, wherein said aerial plant parts or extracts are in the form of a tablet, capsule, chewing formulation, sucking formulation, effervescent formulation, granules, beverage, or instant formulation.

15. The method according to claim 1, wherein the extract is administered in connection with physiologically tolerable auxiliaries.

16. The method according to claim 15, wherein the physiologically tolerable auxiliaries are chosen from a group consisting of carbohydrates, starch degradation products, maltodextrin, glucose syrup, sugars, cellulose, proteins, gum arabic, collagens, and collagen hydrolyzates.

17. The method according to claim 1, wherein the step of identifying a desire to boost cognitive ability comprises identifying a cognitive ability deficit based on testing a patient for cognitive impairment, wherein the testing may include EEG, Mild Cognitive Impairment (MCI) testing, measurement of serotonin uptake inhibition, or behavioral or neurological testing.

18. The method according to claim 1, wherein the extract is prepared using an extractant comprising a mixture of water with 20-50 vol % of alcohols or mixtures of alcohols and ketones wherein said alcohols comprise ethanol or a mixture of ethanol and additional alcohols, said additional alcohols or said ketones are selected from the group consisting of monohydric and polyhydric alcohols and ketones with 1 to 4 carbon atoms.

19. The method of claim 1, wherein the extract is prepared using an extractant consisting essentially of a mixture of water with 20-50 vol % of ethanol.

20. The method of claim 1, wherein the extract is formed by a method consisting essentially of extracting with a mixture of water with 20-50 vol % of ethanol, the method further comprising at least partially removing the extractant and incorporating the extract into a food, a food supplement, a supplementing balanced diet, or a pharmaceutical formulation.

* * * * *